United States Patent
Tweden et al.

(10) Patent No.: US 6,214,041 B1
(45) Date of Patent: *Apr. 10, 2001

(54) TRANSMYOCARDIAL IMPLANT WITH SEPTAL PERFUSION

(75) Inventors: Katherine S. Tweden, Mahtomedi; Timothy R. Conrad, Eden Prairie, both of MN (US)

(73) Assignee: Heartstent Corporation, St. Paul, MN (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

This patent is subject to a terminal disclaimer.

(21) Appl. No.: 09/009,674

(22) Filed: Jan. 20, 1998

(51) Int. Cl.⁷ .................................................... A61F 2/06

(52) U.S. Cl. ......................... 623/1.17; 623/1.1; 623/1.24

(58) Field of Search ........................ 623/1, 3, 1.1, 1.24, 623/1.39, 1.17; 606/194, 198; 472/128; 293/1

(56) References Cited

U.S. PATENT DOCUMENTS

| | | |
|---|---|---|
| 4,546,499 | 10/1985 | Possis et al. . |
| 4,995,857 | 2/1991 | Arnold . |
| 5,306,286 * | 4/1994 | Stack et al. .................... 606/198 |
| 5,409,019 | 4/1995 | Wilk . |
| 5,429,144 | 7/1995 | Wilk . |
| 5,591,223 * | 1/1997 | Lock et al. ........................ 623/1 |
| 5,655,548 | 8/1997 | Nelson et al. . |
| 5,755,682 * | 5/1998 | Knudson et al. .................. 604/3 |

FOREIGN PATENT DOCUMENTS

| | | |
|---|---|---|
| WO 97/13463 | 4/1997 | (WO) . |
| WO 98/06356 | 2/1998 | (WO) . |
| WO 98/08456 | 3/1998 | (WO) . |

OTHER PUBLICATIONS

U.S. application No. 08/882,397, filed Jun. 25, 1997.

U.S. application No. 08/944,313, filed Oct. 6, 1997.

Goldman, A. et al., "Experimental Methods for Producing a Collateral Circulation to the Heart Directly From the Left Ventricle", *J. Thoracic Surg.*, 31(3):364–374 (Mar. 1956).

Massimo, C. et al., "Myocardial Revascularization by a New Method of Carrying Blood Directly From the Left Ventricular Cavity into the Coronary Circulation", *J. Thoracic Surg.*, 34(2):257–264 (Aug. 1957).

Munro, I. et al., "The possibility of myocardial revascularization by creation of a left ventriculocoronary artery fistula", *Thoracic and Cardiovascular Surgery*, 58:(1)25–32 (Jul. 1969).

* cited by examiner

Primary Examiner—Michael J. Milano
Assistant Examiner—Hieu Phan
(74) Attorney, Agent, or Firm—Merchant & Gould P.C.

(57) ABSTRACT

A transmyocardial implant includes a hollow rigid conduit having a first portion and a second portion. The first portion is sized to be received within a coronary vessel lumen. The first portion has an axial dimension aligned with an axis of the vessel. The second portion is sized to extend from the vessel through a myocardium into a heart chamber. The conduit has open first and second ends on axial ends of respective ones of the first and second portions to define a blood flow pathway within an interior of the conduit between the first and second ends. The first portion has at least one radial opening formed therethrough for blood to flow radially outward of the first portion proximally to the first end.

7 Claims, 1 Drawing Sheet

TRANSMYOCARDIAL IMPLANT WITH SEPTAL PERFUSION

BACKGROUND OF THE INVENTION

1. Field of the Invention

This invention pertains to an implant for passing blood flow directly between a chamber of the heart and a coronary vessel. More particularly, this invention pertains to such an implant with an enhance design for providing blood flow to septal perfusing and branching arteries.

2. Description of the Prior Art

Commonly assigned and co-pending U.S. patent application Ser. No. 08/882,397 filed Jun. 25, 1997, now U.S. Pat. No. 5,944,019, entitled "Method and Apparatus for Performing Coronary Bypass Surgery", and filed in the name of inventors Mark B. Knudson and William L. Giese, teaches an implant for defining a blood flow conduit directly from a chamber of the heart to a lumen of a coronary vessel. An embodiment disclosed in the aforementioned application teaches an L-shaped implant in the form of a rigid conduit having one leg sized to be received within a lumen of a coronary artery and a second leg sized to pass through the myocardium and extend into the left ventricle of the heart. As disclosed in the above-referenced application, the conduit is rigid and remains open for blood flow to pass through the conduit during both systole and diastole. The conduit penetrates into the left ventricle in order to prevent tissue growth and occlusions over an opening of the conduit.

Commonly assigned and co-pending U.S. patent application Ser. No. 08/944,313 filed Oct. 6, 1997, now U.S. Pat. No. 5,984,956, entitled "Transmyocardial Implant", and filed in the name of inventors Katherine S. Tweden, Guy P. Vanney and Thomas L. Odland, teaches an implant such as that shown in the aforementioned '397 application with an enhanced fixation structure. The enhanced fixation structure includes a fabric surrounding at least a portion of the conduit to facilitate tissue growth on the exterior of the implant.

Implants such as those shown in the aforementioned applications include a portion to be placed within a coronary vessel and a portion to be placed within the myocardium. When placing a portion of the implant in the coronary vessel, the vessel is axially incised a length sufficient to insert the implant. When placed within the coronary vessel, the implant discharges flow axially into the vessel. The vessel may have multiple branching vessels. For example, in the case of a coronary artery, numerous septal perfusing arteries may branch off of the coronary artery to provide blood to the septal wall. The septal perfusing arteries branch off of the floor of the coronary artery. In addition to these, additional small arteries may branch off of the sides of the coronary artery. Due to the axial length of the implant within the vessel, the wall of the implant may block blood flow to these branching arteries resulting in localized ischemia.

SUMMARY OF THE INVENTION

According to a preferred embodiment of the present invention, a transmyocardial implant is disclosed for establishing a blood flow path through a myocardium between a heart chamber and a lumen of a coronary vessel residing on an exterior of the heart. The implant includes a hollow rigid conduit having a first portion and a second portion. The first portion is sized to be received within the lumen. The first portion has an axial dimension aligned with an axis of the vessel. The second portion is sized to extend from the vessel through the myocardium into the heart chamber. The conduit has open first and second ends on axial ends of respective ones of the first and second portions to define a blood flow pathway within an interior of the conduit between the first and second ends. The first portion has at least one radial opening formed therethrough for blood to flow radially outward of the first portion proximally to the first end.

DESCRIPTION OF THE PREFERRED EMBODIMENT

Figure 1:
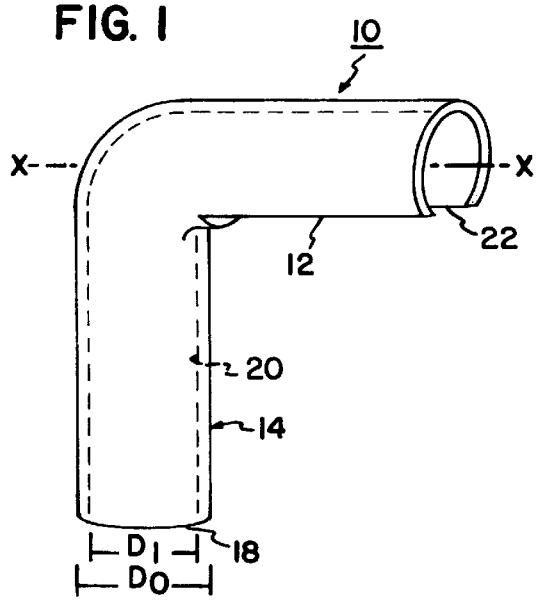
FIG. 1 is a front, top and left-side perspective view of a first embodiment of an implant according to the present invention.

With initial reference to FIG. 1, a conduit 10 is shown in the form of an L-shaped rigid tube. The conduit 10 may be formed of titanium or other rigid biocompatible material such as pyrolytic carbon or may be titanium which is coated with pyrolytic carbon. The material of the conduit 10 is preferably a rigid material in order to withstand contraction forces of the myocardium. By way of example, the tube will have an outside diameter $D_o$ of about 3 millimeters and an internal diameter $D_I$ of about 2 millimeters to provide a wall thickness of about 0.5 millimeters.

Figure 7:
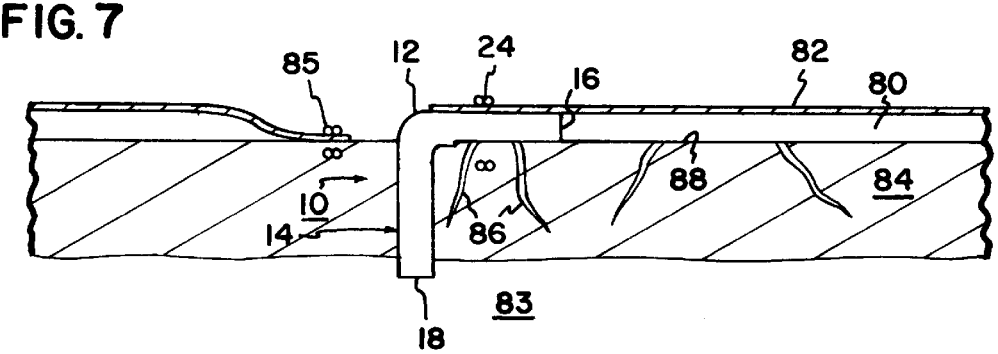
FIG. 7 is a view of the implant of FIG. 1 in place following surgical placement.

The tube 10 has a first portion (or vessel end) 12 which is sized to be received within the lumen of a coronary vessel such as the lumen 80 of a coronary artery 82 illustrated in FIG. 7. The conduit 10 has a second portion (or myocardium end) 14 which extends at a right angle to the axis of portion 12. The second portion 14 is sized to extend from the coronary artery 82 directly through the myocardium 84 and protrude into the left ventricle 86 of a patient's heart. The second portion 14 is sized to have a length sufficient for the portion 14 to protrude into the left ventricle 83.

The vessel end 12 has a first opening 16. The myocardium end 14 has a second opening 18 in communication with an interior 20 of the implant 10. Therefore, blood can freely flow through the implant 10 between the left ventricle 83 and the lumen 80 of the coronary artery 82. Blood flows axially out of opening 16 parallel with the axis of lumen 80.

As discussed more fully in the afore-mentioned commonly assigned and co-pending U.S. patent application Ser. No. 08/882,397, the portion 14 may be provided with tissue-growth inducing material (not shown in the present application) to immobilize the implant 10 within the myocardium 84.

Figure 2:
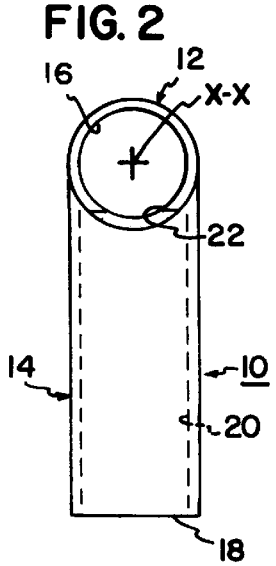
FIG. 2 is a front elevation view of the implant of FIG. 1.
Figure 3:
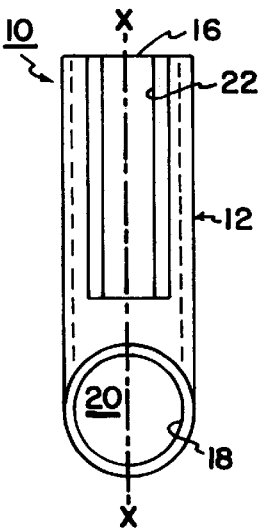
FIG. 3 is a bottom plan view of the implant of FIG. 1.

The implant 10 includes a radial opening 22 on the vessel portion 12 to permit blood to flow radially outwardly from the vessel portion 12 (relative to the longitudinal axis X—X of vessel portion 12). In the embodiment of FIGS. 1–3, the opening 22 is formed by removing the floor of the vessel portion 12 (i.e., that portion of the vessel portion 12 opposing myocardial portion 14). As a result of forming opening 22, septal perfusing arteries may be provided with blood. This is best illustrated in FIG. 7 showing the implant 10 in place. In FIG. 7, the vessel portion 12 is shown residing within a coronary vessel (such as coronary artery 82). The longitudinal axis of the vessel portion is aligned with the axis of the lumen 80. Sutures 24 secure the artery 82 to the vessel portion 12. The proximal portion of the coronary artery is ligated by sutures 85. As shown in FIG. 7, the coronary artery 82 has numerous branching arteries including septal perfusing arteries 86 extending from the floor 88 of the coronary artery 82. With a solid cylindrical vessel portion 12, the arteries 86 within the axial length of the vessel portion 12 will be blocked and deprived of blood. As a result, tissue perfused by these arteries 86 may become ischemic. The opening 22 permits blood to flow radially out of the vessel portion 12 and supply oxygenated blood to these arteries 86.

Figure 4:
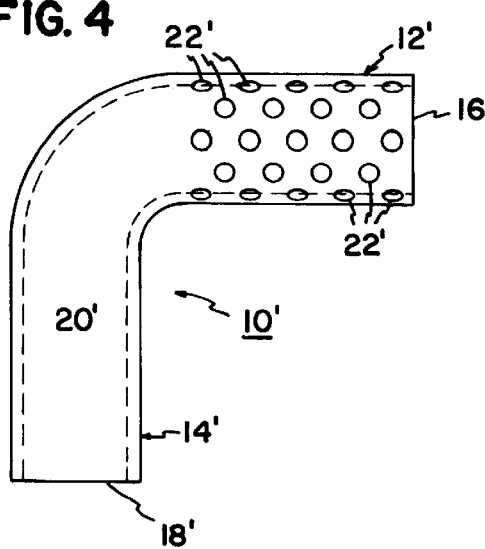
FIG. 4 is a side elevation view of a second embodiment of an implant according to the present invention.
Figure 5:
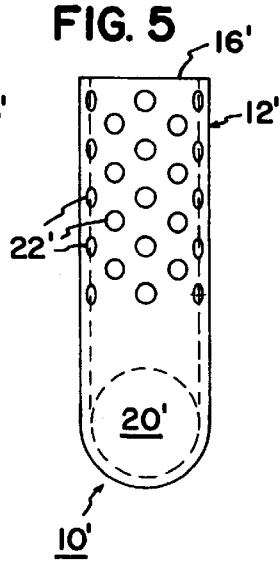
FIG. 5 is a top plan view of the implant of FIG. 4.
Figure 6:
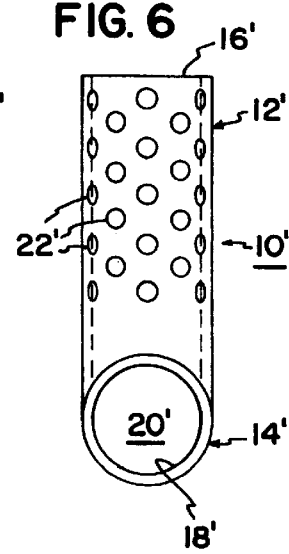
FIG. 6 is a bottom plan view of the implant of FIG. 1.

FIGS. 4–6 illustrate an alternative embodiment implant 10' (all similar elements numbered identically with the addition of an apostrophe). Unlike the embodiment of implant 10 where the opening 22 is formed by removing the base of the vessel portion 12, the implant 10' is provided with a plurality of holes 22' perforating the vessel portion 12' to permit flow radially out of the vessel portion 12'. The holes 22' extend the axially length of the vessel portion 12' and surround the cylindrical wall of the vessel portion 12'. In addition to supplying blood to septal perfusing arteries 86 extending from the floor 88 of the artery 82, the holes 22' supply blood to branching arteries (not shown) which may extend from the sides of the coronary artery 82.

In addition to the open base 22 and holes 22', openings through the vessel portion 12 can be formed in other ways. For example, the vessel portion 12 can be formed of cross-hatched material (similar to stent construction) with areas between the material of the portion 12 defining the openings through the vessel portion 12.

While not a preferred embodiment, the myocardial portion 14 may be provided with holes to permit radial flow directly into the myocardium 84. This is consistent with well-known transmyocardial revascularization techniques attempting to supply blood to the myocardium directly by forming holes through the myocardium in communication with the left ventricle. However, such a design is not preferred since the myocardium 84 is thrombogenic and such holes may result in thrombus occluding the implant 10, 10'.

Having disclosed the present invention in a preferred embodiment, it will be appreciated that modifications and equivalents may occur to one of ordinary skill in the art having the benefits of the teachings of the present invention. It is intended that such modifications shall be included within the scope of the claims which are appended hereto.

What is claimed:

1. A transmyocardial implant for establishing a blood flow path through a myocardium between a heart chamber and a lumen of a coronary vessel residing on an exterior of said wall, said implant comprising:

a hollow rigid conduit having a rigid and non-expansible first portion and a rigid and non-expansible second portion coupled to one another;

said first portion sized to be received within said lumen, said first portion having an axial dimension adapted to be aligned with an axis of said vessel;

said second portion sized to extend from said vessel through said myocardium into said chamber;

said conduit having open first and second ends on axial ends of respective ones of said first and second portions to define a blood flow pathway within an interior of said conduit between said first and second ends; and said first portion and second portion are disposed at an angle relative to one another and with said first portion having a base opposing said second portion, said base having an axially extending hole extending substantially through an axial length of said base for blood to flow radially through said axially extending hole in addition to flowing axially out of said first open end, a cylindrical wall of said first portion other than said base being substantially solid;

said second portion having a solid wall blocking fluid flow through said second portion between said blood flow pathway and said myocardium throughout an entire thickness of said myocardium.

2. A transmyocardial implant for establishing a blood flow path through a myocardium between a heart chamber and a lumen of a coronary vessel residing on an exterior of said wall, said implant comprising:

a hollow rigid L-shaped conduit having a rigid and non-expansible first portion and a rigid and non-expansible second portion;

said first portion sized to be received within said lumen, said first portion having an axial dimension adapted to be aligned with an axis of said vessel;

said second portion sized to extend from said vessel through said myocardium into said chamber and said second portion having a solid wall blocking fluid flow through said second portion between said blood flow pathway and said myocardium throughout an entire thickness of said myocardium;

said conduit having open first and second ends on axial ends of respective ones of said first and second portions to define a blood flow pathway within an interior of said conduit between said first and second ends; and said first portion having at least one radial opening formed therethrough for blood to flow radially outward of said first portion proximally to said first end;

said first portion having a radially rigid cylindrical wall and further having a plurality of perforations formed through said cylindrical wall an arcuate transition between said first and second portions with said arcuate transition having a solid-wall construction.

3. A transmyocardial implant for establishing a blood flow path through a myocardium between a heart chamber and a lumen of a coronary vessel residing at an exterior of said wall, said implant comprising:

a hollow rigid conduit having a first portion and a second portion;

said first portion sized to be received within said lumen, said first portion having an axial dimension aligned with an axis of said vessel;

said second portion sized to extend from said vessel through said myocardium into said chamber;

said conduit having open first and second ends on axial ends of respective ones of said first and second portions to define a blood flow pathway within an interior of said conduit between said first and second ends; and said first portion having at least one radial opening formed therethrough for blood to flow radially outward of said first portion proximally to said first end.

4. The transmyocardial implant of claim 3, wherein the second portion of the conduit has a solid wall construction free of any radial openings.

5. The transmyocardial implant of claim 4, further comprising a bend between the first and second portions.

6. The transmyocardial implant of claim 5, wherein the first portion defines a plurality of the radial openings.

7. The transmyocardial implant of claim 6, wherein both the first and second portions are rigid.

* * * * *

UNITED STATES PATENT AND TRADEMARK OFFICE
CERTIFICATE OF CORRECTION

PATENT NO. : 6,214,041 B1
DATED : April 10, 2001
INVENTOR(S) : Tweden et al.

It is certified that error appears in the above-identified patent and that said Letters Patent is hereby corrected as shown below:

Column 3,
Line 50, line beginning "said first portion ..." and remaining paragraph should be indented.
Line 53, line beginning "said second portion ..." and remaining paragraph should be indented.
Line 55, line beginning "said conduit ..." and remaining paragraph should be indented.
Line 58, "ends; and" should read -- ends; --
Line 65, "end," should read -- end; --

Column 4,
Line 26, "second ends;" should read -- second ends, --
Line 33, after "cylindrical wall" insert -- ; and --

Signed and Sealed this

Twelfth Day of August, 2003

JAMES E. ROGAN
*Director of the United States Patent and Trademark Office*